(12) United States Patent
Lee

(10) Patent No.: US 6,243,609 B1
(45) Date of Patent: Jun. 5, 2001

(54) TREATMENT MAT

(76) Inventor: Hwan-Sung Lee, Poonglim 2nd Apt. #404,104, Kangnam-ku, Seoul (KR)

( * ) Notice: Subject to any disclaimer, the term of this patent is extended or adjusted under 35 U.S.C. 154(b) by 0 days.

(21) Appl. No.: 09/482,828

(22) Filed: Jan. 14, 2000

(30) Foreign Application Priority Data

Jul. 6, 1999 (KR) .................................................. 99-26985

(51) Int. Cl.$^7$ ...................................................... A61F 2/00
(52) U.S. Cl. ............................ 607/100; 607/90; 607/154
(58) Field of Search ........................ 607/90, 91, 98–102, 607/154, 156; 606/201, 204, 237–245

(56) References Cited

U.S. PATENT DOCUMENTS

| | | | |
|---|---|---|---|
| 4,316,474 | * | 2/1982 | Spethmann ........................... 607/156 |
| 4,397,314 | * | 8/1983 | Vaguine . |
| 4,535,784 | * | 8/1985 | Rohlicek et al. . |
| 6,096,066 | * | 8/2000 | Chen et al. .............................. 607/88 |

* cited by examiner

*Primary Examiner*—Linda C. M. Dvorak
*Assistant Examiner*—Roy Gibson
(74) *Attorney, Agent, or Firm*—Jacobson, Price, Holman & Stern, PLLC

(57) ABSTRACT

A treatment mat includes: a mat foldable at the one side thereof and centrally provided with a longitudinal groove; a hyperthermo-therapeutical apparatus moving along a rail provided in the longitudinal groove of the mat; a mechanism for conveying the hyperthermo-therapeutical apparatus; a control panel for controlling the conveying mechanism, and a control unit for controlling the position of the hyperthermo-therapeutical apparatus.

1 Claim, 1 Drawing Sheet

TREATMENT MAT

BACKGROUND OF THE INVENTION

1. Field of the Invention

The present invention relates generally to a treatment mat and, more particularly, to a treatment mat designed to apply a compress and infrared radiation to a vertebral acupuncture point of man and thereby enhance the curative effect.

2. Description of the Related Art

A conventionally used hyperthermo-therapeutical apparatus includes a heater for emitting heat and a control box having a control panel for controlling the heater. The hyperthermo-therapeutical apparatus is disposed to apply a hot compress to the vertebral acupuncture point of a patient lying on the floor and, in order to treat another part of the body, moved onto the interested part with reference to a therapeutical guide book to apply a compress.

Such a hyperthermo-therapeutical apparatus, however, has to be moved over the body of a patient lying on the floor. Also, the hyperthermo-therapeutical apparatus is so high as to make the vertebra bend backward.

Furthermore, all the weight of the patient is imposed on the small compress point of the hyperthermo-therapeutical apparatus so that excessive pressure is transferred to the acupuncture point supporting the hyperthermo-therapeutical apparatus. For this reason, the hyperthermo-therapeutical apparatus cannot be employed to treat the patient for a long time.

SUMMARY OF THE INVENTION

Accordingly, it is an object of the present invention to provide a mat type therapeutical apparatus which is designed to apply a compress to the vertebral acupuncture point of a patient with a hyperthermo-therapeutical apparatus moving in the horizontal direction with respect to the center of the mat for the purpose of use convenience.

It is another object of the present invention to provide a treatment mat whose center is provided with a groove for mounting a hyperthermo-therapeutical apparatus slightly projecting from the surface of the mat, thereby preventing an excessive force imposed on the vertebra of the patient.

It is further another object of the present invention to provide a treatment mat designed to move a hyperthermo-therapeutical apparatus onto a desired part of a lying patient for the purpose of use convenience.

To achieve the above object of the present invention, there is provided a treatment mat including: a mat foldable at the one side thereof and centrally provided with a longitudinal groove; a hyperthermo-therapeutical apparatus moving along a rail provided in the longitudinal groove of the mat; means for conveying the hyperthermo-therapeutical apparatus; a control panel for controlling the conveying means; and a control unit for controlling the position of the hyperthermo-therapeutical apparatus.

BRIEF DESCRIPTION OF THE DRAWINGS

The above and other objects, features and advantages of the present invention will become more apparent from the following detailed description when taken in conjunction with the accompanying drawings in which.

DETAILED DESCRIPTION OF THE PREFERRED EMBODIMENT

A preferred embodiment of the present invention will be described below with reference to the accompanying drawings. In the following description, well-known functions or constructions are not described in detail since they would obscure the invention in unnecessary detail.

Figure 1:
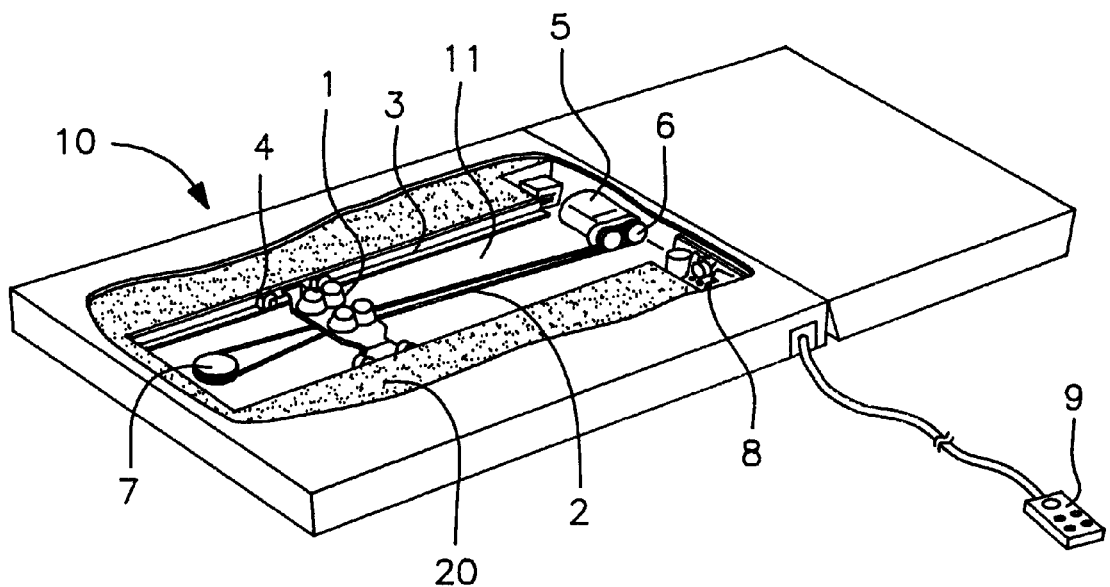
FIG. 1 is a partial perspective of the present invention.
Figure 2:
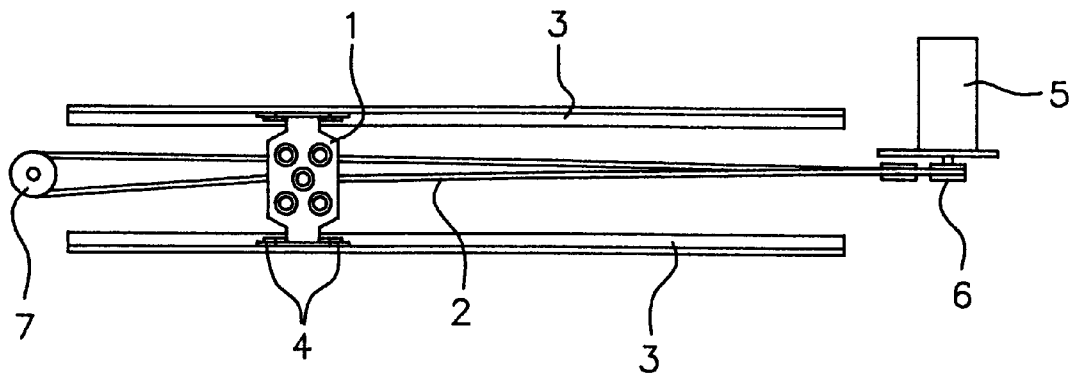
FIG. 2 is a plan view of a position shifter of a hyperthermo-therapeutical apparatus in the present invention.

Now, reference will be made as to a description of the construction of the present invention. Referring to FIG. 1, the present invention includes: a mat 10 foldable at the one side thereof and centrally provided with a longitudinal groove 11; a hyperthermo-therapeutical apparatus 1 moving along a rail 3 disposed in the longitudinal groove 11 of the mat 10; a conveyer for moving the hyperthermo-therapeutical apparatus 1; a control panel 8 for controlling the conveyer; and a control unit 9 for controlling the position of the hyperthermo-therapeutical apparatus 1. The present invention further includes: a pair of wheels 4 provided on both lateral sides of the hyperthermo-therapeutical apparatus I to be moved along the rail 3 provided in the longitudinal groove 11 of the mat 10; a motor 5 for driving the conveyer according to a signal output from a circuit of the control panel 8; and a wire 2 connecting a pulley 6 at the motor side to an idle pulley 7 at the one side of the mat 10. The end of the wire 2 is associated with the hyperthermo-therapeutical apparatus.

In the operation of the above-constructed present invention, as a patient lies on the mat 10, the hyperthermo-therapeutical apparatus 1 installed in the center of the mat 10 applies a hot compress to the vertebral acupuncture point of the patient and, simultaneously, the far infrared radiation emitted from the hyperthermo-therapeutical apparatus 1 gives a wave motion to the artery of the vertebra to help blood circulation and enhance the curative effect. To describe this operation in further detail, as the patient lies on the treatment mat 10 to which power is applied, the hyperthermo-therapeutical apparatus 1 installed in the longitudinal groove 11 of the mat 10 and projecting slightly higher than a lateral cushion 20 applies a compress to the vertebra due to the weight of the patient.

As the vertebral acupuncture point is compressed to provide the finger-pressure curative effect and stimulate a nerve connected to the acupuncture point. In the meantime, the lamp provided in the hyperthermo-therapeutical apparatus not only emits heat to apply a hot compress to the acupuncture point but also provides far infrared radiation from a jade used as a cap of the hyperthermo-therapeutical apparatus, thus helping blood circulation and maximizing the curative effect.

Since a long-term stimulus on one acupuncture point may adversely affect another part of the body, the hyperthermo-therapeutical apparatus 1 is moved to stimulate another acupuncture point. At this time, the patient can shift the position of the hyperthermo-therapeutical apparatus 1 with buttons of the control unit 9.

The motor 5 operates to move the hyperthermo-therapeutical apparatus 1 as long as the patient presses the buttons of the control unit 9. With the motor 5 driven, the one end of the wire 2 wound around the pulley 6 on the motor side pulls the hyperthermo-therapeutical apparatus 1 coupled thereto as the pulley 6 rotates, so that the wheels 4 on the lateral sides of the hyperthermo-therapeutical apparatus 1 move long the rail 3 to a predefined position.

The hyperthermo-therapeutical apparatus 1 completely moved to the one side of the mat 10 pushes the arm of a micro switch provided at the end of the raid 3 to turn the micro switch on and suspend the operation of the motor 5. As a result, the direction of the current applied to the motor 5 is reversed to provide reverse rotation of the motor 5. Thus reversed running direction of the hyperthermo-therapeutical apparatus 1 makes the hyperthermo-therapeutical apparatus 1 move in the opposite direction.

Although it has been described in the above embodiment that the hyperthermo-therapeutical apparatus is moved manually as long as a desired distance, the present invention also employ a built-in microcomputer to move the hyperthermo-therapeutical apparatus by a desired distance and apply a compress to the acupuncture point for a predetermined period of time. After an elapse of the predetermined time, the hyperthermo-therapeutical apparatus is moved as long as a desired distance to stimulate another acupuncture point of the body.

As described above, the present invention is convenient to use because the patient lying on the treatment mat can stimulate a desired acupuncture point and the hyperthermo-therapeutical apparatus slightly projecting from the treatment mat imposes no excessive pressure on the vertebra of the patient.

Furthermore, a patient who has a difficulty in moving can easily have a compress treatment by moving the hyperthermo-therapeutical apparatus to a desired position in an automatic manner. After the completion of treatment, the treatment mat can be conveniently stored with the one side thereof folded.

While the invention has been shown and described with reference to a certain preferred embodiment thereof, it will be understood by those skilled in the art that various changes in form and details may be made therein without departing from the spirit and scope of the invention as defined by the appended claims.

What is claimed is:

1. A treatment mat comprising:

a mat foldable at the one side thereof and centrally provided with a longitudinal groove;

a hyperthermo-therapeutical apparatus moving along a rail provided in the longitudinal groove of the mat;

means for conveying the hyperthermo-therapeutical apparatus;

a control panel for controlling the conveying means; and a control unit for controlling the position of the hyperthermo-therapeutical apparatus.

\* \* \* \* \*

(12) EX PARTE REEXAMINATION CERTIFICATE (4958th)
United States Patent
Lee

(10) Number: US 6,243,609 C1
(45) Certificate Issued: Jul. 6, 2004

(54) TREATMENT MAT

(75) Inventor: Hwan-Sung Lee, Poonglim 2nd Apt. #404,104, Kangnam-ku , Seoul (KR)

(73) Assignee: Hwan-Sung Lee, Seoul (KR)

Reexamination Request:
  No. 90/006,165, Dec. 26, 2001

Reexamination Certificate for:
  Patent No.: 6,243,609
  Issued: Jun. 5, 2001
  Appl. No.: 09/482,828
  Filed: Jan. 14, 2000

(30) Foreign Application Priority Data

Jul. 6, 1999 (KR) .............................. 99-26985

(51) Int. Cl.$^7$ ................................. A61F 2/00
(52) U.S. Cl. .................. 607/100; 607/90; 607/154

(56) References Cited

U.S. PATENT DOCUMENTS 4,694,515 A   9/1987   Rogers, Jr.
5,887,589 A   3/1999   Hogan
5,943,965 A   8/1999   Riach et al.

FOREIGN PATENT DOCUMENTS

JP   60-180431      11/1985
KR   10-0159994     7/1997
KR   20-1997-014721  1/1999

*Primary Examiner*—Lee S. Cohen

(57) ABSTRACT

A treatment mat includes: a mat foldable at the one side thereof and centrally provided with a longitudinal groove; a hyperthermo-therapeutical apparatus moving along a rail provided in the longitudinal groove of the mat; a mechanism for conveying the hyperthermo-therapeutical apparatus; a control panel for controlling the conveying mechanism, and a control unit for controlling the position of the hyperthermo-therapeutical apparatus.

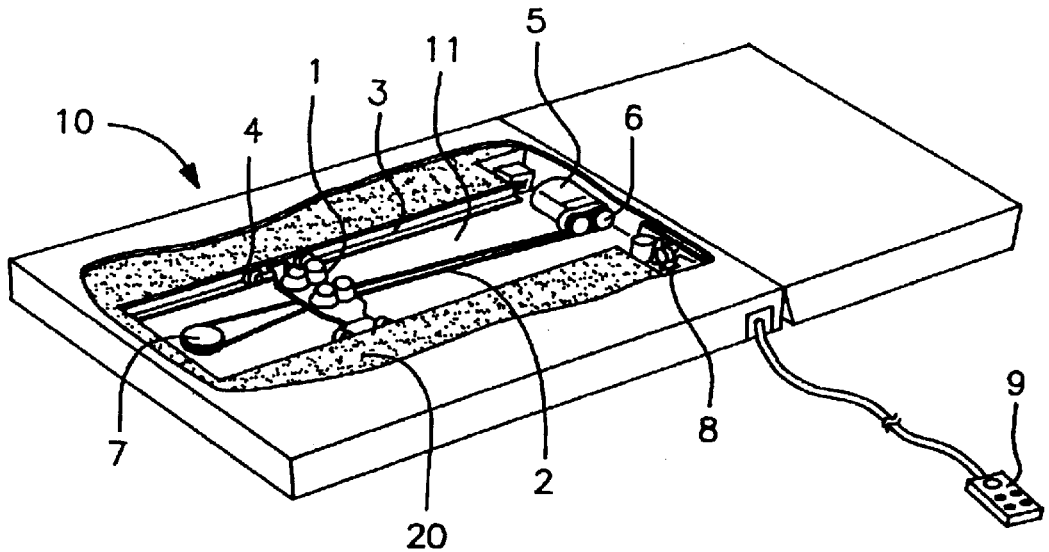

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

\* \* \* \* \*